United States Patent [19]
Keating et al.

[11] Patent Number: 5,185,242
[45] Date of Patent: Feb. 9, 1993

[54] METHOD FOR LYSING MYCOBACTERIA USING ACHROMOPEPTIDASE

[75] Inventors: William E. Keating, Durham; Jillian A. Robson, Pittsboro, both of N.C.

[73] Assignee: Becton Dickinson and Company, Franklin Lakes, N.J.

[21] Appl. No.: 720,076

[22] Filed: Jun. 24, 1991

[51] Int. Cl.$^5$ .................. C12Q 1/68; C12N 9/52; C12P 19/34; C07H 21/00
[52] U.S. Cl. ........................... 435/6; 435/220; 435/253.1; 435/270; 435/91; 536/23.1
[58] Field of Search .............. 435/6, 220, 91; 536/27

[56] References Cited

U.S. PATENT DOCUMENTS 4,900,677  2/1990  Hewitt ........................... 435/259

FOREIGN PATENT DOCUMENTS 0151783  8/1985  European Pat. Off. .
0261955  3/1988  European Pat. Off. .
0288618  11/1988  European Pat. Off. .

OTHER PUBLICATIONS

Zinsser Microbiology, 1984, Joklik et al., eds. Appleton-Century-Crofts, Norwalk, Conn., p. 12.
D. L. Whipple et al., *J. Clin. Microbiol.* 25:1511 (1987).
R. N. Picken et al., *Molecular and Cellular Probes* 2:289 (1988).
S. S. Hurley et al., *J. Clin. Microbiol.* 25:2227 (1987).
T. Ezaki et al., *J. Clin. Microbiol.* 16:844 (1982).

*Primary Examiner*—Amelia B. Yarbrough
*Assistant Examiner*—Lisa Bennett
*Attorney, Agent, or Firm*—Brian K. Stierwalt

[57] ABSTRACT

The invention provides a rapid method for lysing Mycobacteria. In one embodiment is provided a method for lysing Mycobacteria which comprises exposing the bacteria to a lysis effective amount of the enzyme achromopeptidase.

The method of the invention is particularly advantageous since only one step is involved, it is expedient compared to prior methods, and little instrumentation is necessary. By practicing the present invention it is possible to lyse Mycobacteria with minimal effort. In addition, practicing the invention results in liberating cellular components including deoxyribonucleic acid (DNA) from Mycobacteria. Not only is DNA liberated, but the DNA is suited for subsequent analysis by way of probe hybridization, restriction enzyme analysis, and the like.

42 Claims, No Drawings

METHOD FOR LYSING MYCOBACTERIA USING ACHROMOPEPTIDASE

FIELD OF THE INVENTION

The invention is in the field of molecular biology. In particular the invention is in the area of cell lysis. Most particularly the invention is a method for lysis of Mycobacteria.

BACKGROUND OF THE INVENTION

Mycobacteria are a large, diverse, and widely distributed family of aerobic, nonsporulating, nonmotile bacilli that have a high cell-wall lipid content and a slow growth rate. Members of the Mycobacterium genus vary tremendously in virulence. Some Mycobacteria are harmless while others like *M. tuberculosis* are significant pathogens. Mycobacterium species are differentiated by their growth rate, pigment production, animal virulence, and biochemical reactivity.

Many detection methods for determining the presence of pathogenic organisms such as those in the Mycobacteriaceae family relay on the lysis of those organisms. However, the lysis procedures for Mycobacteriaceae are laborious and time consuming. For example, chemical disruption of Mycobacteria is tedious and can take days. European Patent Application number 87 303641.2 discloses a method for releasing DNA or RNA from Mycobacteria which comprises the use of minute beads in combination with a sonicating bath. S. Hurley et al., *J. Clin Microbiol.* 25:2227 (1987) disclose a method for lysing mycobacteria that uses a mini-bead-beater cell disrupter and zirconium beads.

Recent advances in mycobacterial genetics and increased interest in opportunistic pathogens in patients like those suffering from acquired immunodeficiency syndrome have focused attention to the fact that a procedure for rapid lysis of Mycobacteriaceae is needed. It would be advantageous to have a process for lysing Mycobacteria that is simple, fast, and not disruptive to the material desired from the lysis.

SUMMARY OF THE INVENTION

The present invention provides a process for lysing Mycobacteria that is simple, fast, and not disruptive to the material desired from the lysis. In one embodiment is provided a process for lysing Mycobacteria which comprises exposing the bacteria to a lysis effective amount of the enzyme achromopeptidase.

Further embodiments include isolating specific cellular components liberated from lysis of Mycobacteria using the method of the invention.

Specific embodiments also include the additional step of isolating nucleic acid from Mycobacteria and amplifying nucleic acid obtained from practicing the method of the present invention.

Other embodiments include the addition of a Mycobacteria identifying agent to the lysed Mycobacteria to identify the presence of Mycobacteria.

Embodiments also include kits comprising lysis effective amounts of achromopeptidase and a Mycobacteria identifying agent.

The method of the invention is particularly advantageous since only one step is involved, it is expedient compared to prior processes, and little instrumentation is necessary. By practicing the method of the invention it is possible to lyse Mycobacteria with minimal effort. In addition, practicing the invention results in liberating deoxyribonucleic acid (DNA) from Mycobacteria. Not only is DNA liberated, but the DNA is liberated in relative uniform size, rendering the DNA well suited for subsequent analysis by way of probe hybridization, restriction enzyme analysis, amplification, and the like.

As used in this document, "lysis effective amount of achromopeptidase" refers to that amount of achromopeptidase which liberates intracellular components such as DNA, RNA, and the like.

DETAILED DESCRIPTION OF THE INVENTION

The present invention allows for the lysis and resultant liberation of DNA and cellular material from Mycobacteria. The enzyme employed in the process is achromopeptidase, also known as lysyl endopeptidase. The enzyme is readily available from a variety of sources, including commercial availability from vendors. The enzyme is also obtainable by isolation from the organism *Achromobacter lyticus*.

The exposure of Mycobacteria to the enzyme achromopeptidase is advantageous over known methods for lysis of Mycobacteria which involve the use of caustic chemicals, time consuming culturing, and mechanical methods which use the French press. the Hughes press, sonicating probes, bath sonicators, freeze thawing, glass beads, the Ribi pressure cell, and the like.

Although numerous enzymes and procedures exist for lysing a variety of organisms, the application of the enzyme achromopeptidase to lyse Mycobacteria is unique. Mycobacteria are notorious for their inability to readily lyse. Those procedures that do result in lysis of Mycobacteria also generally destroy the contents of the cell that were desired. If the contents of the cell were not destroyed from the lysis procedure, it was generally the result of timely and laborious protocols Mycobacteria are extremely resistant to physical stress and can be subjected to concentration and digestion procedures that kill ordinary bacteria. Thus, it is unexpected that the enzyme achromopeptidase, which can lyse less strenuous bacteria, can also lyse the extraordinarily lysis resistant Mycobacteria. It is also unexpected that achromopeptidase works so well in lysing Mycobacteria because other, more stringent conditions, do not work. However, the practice of the present invention results in Mycobacteria lysis and subsequent yield of useable pieces of DNA that are suitable for use for a variety of purposes such as detection methods and amplification, as well as liberating RNA and other cellular components.

Subsequent use of cellular components liberated from lysis include identification of Mycobacteria and amplification of nucleic acid by means such as polymerase chain reaction, ligase chain reaction, and the like. Identification can take place by means of Mycobacteria identifying agents. Identifying agents refers to those agents suitable for identifying Mycobacteria which include nucleic acid probes including deoxyribonucleic acid and ribonucleic acid, and the like.

The use of probes, for example, for identifying the presence of a particular Mycobacterium can be employed in a one step identification method. For example, once a sample is obtained, such as a sputum sample, the sputum is digested with a liquifying agent like N Acetyl-L Cysteine (NALC). After digestion and concentration a lysis effective amount of achromopeptidase is added to the sample, followed by the addition of an identifying agent. The presence of Mycobacteria can then be detected by a variety of means, depending on the marker (e.g., signal to be detected) chosen for use with the identifying agent. The means for identification of the presence of Mycobacteria is usually dictated by the identifying agent employed. For example, nucleic acid probes (e.g., specific for a Mycobacteria species) are typically labeled with $^{125}I$, $^{32}P$, fluorescent markers, and the like. The marker is then detected, which detection is an indication that the particular Mycobacteria is present. Other means for detection include Southern Blot analysis, electrophoretic gel visualization, and the like.

The Mycobacteria identifying agent and achromopeptidase can be conveniently provided in the form of a kit. Such a kit comprises at least one type of identifying agent and a lysis effective amount of achromopeptidase. Specific kits comprise identifying agents for any Mycobacteria or specific Mycobacterium. Specific kits also comprise particular Mycobacteria identifying means such as nucleic acid probes or antibodies. And, the means by which the identifying agent is detected can also be specific, for example, the agent can be designed for fluorescence, radioactive, and chemiluminescence detection and, if necessary, depending on sample requirements, liquification agents, isolation agents, and the like can be included in the kit.

The process of the invention can be employed once the Mycobacteria have been obtained in the form of a sample such as sputum, or an isolated form. Mycobacteria are isolated from a variety of sources including feces, sputum, urine, serum, tissue, other body fluids or obtained from public or private culture collections, and the like. Mycobacteria obtained from the various sources are typically cultured, which is very time consuming, reaching three to six weeks culture time. However, by practicing the method of the invention, the need to culture can be eliminated. If culturing is not desired, the cells are generally first isolated from the source by conventional sample processing methods then usually pelleted by centrifugation and put into a cell suspension. The Mycobacteria in the cell suspension are then lysed. Lysis by the present invention comprises the addition of a lysis effective amount of achromopeptidase to the cells. The achromopeptidase does not have to be pure, and preferably is impure. This is advantageous in that purification steps are eliminated prior to use of the enzyme, and attention to contamination is eased. Preferably the enzyme is present in about 50 units to about 1000 units, most preferably the enzyme is present in about 100 units to about 300 units.

The process of the invention could be practiced without culturing. Unpurified biological samples from sputum, feces, tissue, blood, serum, and the like, can be lysed by practicing the invention and in the same sample could be identified with a Mycobacteria identifying agent. Thus the method comprises a simplified means for detecting Mycobacteria in a clinical, biological, food or environmental sample.

A typical protocol for lysing Mycobacteria with achromopeptidase comprises centrifugation of a sample of Mycobacteria for a brief amount of time (e.g., about five minutes) and discarding the resultant supernatant. The pellet of Mycobacteria can then be reconstituted in a buffered mixture of the achromopeptidase enzyme. Any suitable buffer will work. Suitable buffers include Trizma and NaCl, and Borate and NaCl After a brief incubation (e.g., about thirty minutes) at about room temperature to about 50 degrees Centigrade lysis is complete and the liberated cellular contents can be conveniently isolated by conventional methods. Conventional methods for isolating DNA include phenol:chloroform extractions, glass binding with subsequent elution, and the like. Examples of conventional protocols for isolating DNA are found in references such as T. Maniatis et al., *Molecular Cloning: A Laboratory Manual* (*Cold Spring Harbor Lab*) (1982) and Boom et al., *J. Clin. Micro* 28:495 (1990).

The fact that the process of the present invention liberates DNA in utilizable size is significant. Although prior methods obtained lysis of Mycobacteria through laborious and time consuming methodology, the DNA liberated was generally not of useable size (it was degraded into pieces too small for subsequent use). It is important that liberated DNA be of sufficient size to allow for its subsequent use in detection procedures. Thus, despite the fact that a variety of lysis procedures obtain DNA, it is important to obtain DNA in useful quantity and size.

Important Mycobacteria that can be lysed by practicing the present invention include *M. avium, M. intracellularae, M. gordonae, M. tuberculosis, M. kansasii, M. fortuitum, M. chelonae, M. bovis, M. scrofulaceum, M. paratuberculosis, M. marinum, M. simiae, M. szulgai, M. intracellulare, M. xenopi, M. ulcerans, M. leprae, M. lepraemurium, M. smegmatis, M. flavescens, M. terrae, M. nonchromogenicum, M. malmoense, M. asiaticum, M. vaccae, M. gastri, M. triviale, M. haemophilum, M. africanum, M. thermoresistable,* and *M. phlei.* Several of the Mycobacteria are pathogenic. For example, *M. tuberculosis,* which already infects two billion people and infects an additional seven to nine million people each year, is an important Mycobacteria from an epidemiologic and clinical viewpoint In addition, *M. averium, M. bovis, M. intracellularae, M. africanum, M. leprae, M. chelonae, M. paratuberculosis,* and *M. marinum,* are also significant from an epidemiological and clinical viewpoint.

The practice of the present invention provides a rapid and simple lysis procedure for Mycobacteria that provides DNA, RNA and cellular components for subsequent use in a variety of detection procedures.

The following examples illustrate the specific embodiments of the invention described in this document. As would be apparent to skilled artisans, various changes and modifications are possible and are contemplated within the scope of the invention described.

EXAMPLES

EXAMPLE 1

Purpose

This experiment compares purified achromopeptidase enzyme to a crude product using equivalent amounts (by weight and by enzyme units) with Bactec cultures.

Materials

"Crude" achromopeptidase—(Sigma, St. Louis, Mo., cat# A-7550 lot# 127F-68391)

"Purified" achromopeptidase—(Sigma cat# A-3422 lot# 630H-0438)

Pooled Bactec cultures of *M. tuberculosis* (strain H37RV American Type Culture Collection (ATCC)) and *M. fortuitum*

Amresco (Solon, OH) TE (10 mM TRIS-HCl, 1 mM EDTA, pH 8.0) buffered phenol/chloroform (1:1)

Procedure

Isolate 2 ml pellets of *M. tuberculosis* and *M. fortuitum* (4 pellets for each species).

Reconstitute pellets according to the following recipes:

"Crude" Achromopeptidase: 1 mg/ml 550 units/mg, 100 units = 182 μL
"Purified" Achromopeptidase: 1 mg/ml 25,000 units/mg, 100 units = 4μL

1 50 ug Crude Achromopeptidase = 50 μL + 450 μL TRizma 9.0 (pre pH adjusted mixes of TRIS-HCl + TRIS hydroxide to give a set pH) (27 units)
2 50 ug Purified Achromopeptidase = 50 μL + 450 μL TRizma 9.0 (1250 units)
3 100 units Crude Achromopeptidase = 182 μL + 318 μL TRizma 9.0 (182 μg)
4 100 units Purified Achromopeptidase = 4 μL + 496 μL TRizma 9.0 (4 μg)

Vortex all samples, then incubate at 50° C. for 30 minutes.

Perform 2 phenol/chloroform extractions, then ethanol. Precipitate and dry samples in speed-vac before reconstituting pellets in 10 μl TE buffer and running sample on 1% agarose gel.

Samples were stained with 1 ug/ml ethidium bromide and visualized under UV light.

The results (band intensity) show that the crude enzyme works better than the partially purified enzyme. More DNA was released from *M. tuberculosis* and *M. fortuitum* with the crude enzyme.

EXAMPLE 2

Purpose

This experiment examines 8 species of Mycobacteria with 100 units of achromopeptidase. The Mycobacteria are:
- *M. avium*
- *M. scrofulaceum*
- *M. intracellularae*
- *M. gordonae*
- *M. tuberculosis*
- *M. kansasii*
- *M. fortuitum*
- *M. chelonae*

Materials

Crude achromopeptidase
8 pooled Bactec cultures of Mycobacteria
Amresco TE buffered phenol/chloroform Procedure Isolate 2 ml pellets of each species
Reconstitute each pellet into 500 μL TRizma 9.0
Incubate for 30 minutes at 50° C. with 100 units achromopeptidase (36 μL or 5 mg/ml stock = 2750 units/mg)
Vortex while incubating (2 or 3 times)
Perform 2 phenol/chloroform extractions on each
Ethanol precipitate samples overnight at −20° C.
Spin ½ hour at 4° C., remove ethanol, dry pellets in virtis lyophilizer for 30 minutes. Resuspend in 17 μL TE and 3 μL loading dye
Electrophorese in 1% agarose. Ethidium Bromide stain 10 minutes then visualize under UV light Results indicate that DNA of same size is seen for all species (gel visualization).

EXAMPLE 3

Purpose

To screen a series of enzymes for lysis efficiency of *M. tuberculosis*.

Materials

*M. tuberculosis*
Lysozyme (Sigma cat# L-6876 lot# 39F-8210)
Achromopeptidase (Sigma cat# A-3547 lot# 88F-0799)
Lipoxidase (Sigma cat# L-7395 lot# 118F-05421)
Mixed Glycosidase A (From *C. Lamdas*, Sekagaku, Miles, Elkhart, Ind., lot# 8L84803)
Zymolase 20T (Sekagaku/Miles cat# 32 092 1 lot#2)
Mixed Glycosidase B (From *T. Cornelius*, Sekagaku lot# ET84701)
Lysing Enzymes A (From *Tricoderma harzanium* Sigma cat# L-2265 lot# 36F-080
Lysing enzymes B (From *Rhizoctonia Solani* Sigma cat# L-8757 lot# 468-0273
Phospholipase A (Sigma cat# D-6534 lot# 129F-8005)
Lipase (Sigma cat# L-4384 lot# 88F-02081)
Mutanolysin (Sigma cat# M 9901 lot# 98F-68211)
Achromopeptidase/Mutanolysin cocktail (10 mg/ml/1 mg/ml)
Gen Probe (San Diego, Calif.) lysing reagent tube (lot# 92084 exp. 12/16/91)
1:1 Phenol/chloroform (TRIS saturated BRL 55090A lot# 71209/Baxter B&J cat# 67-66 3 lot# A W342
Ethanol (Fisher (Pittsburgh, Pa.) E-575 500 lot# 887309) 70%
3M sodium acetate pH 5.5
Lyophillizer (Savant speed vaccuum concentrator model
TE buffer
Other electrophoresis equipment Procedure 1) Into 13 tubes, 2 ml of pelleted *M. tuberculosis* was placed in each after being decanted.

2) To each portion was added 90 μL H$_2$O (except the GEN probe tube, which received 100 μL) and 10 μL of the enzyme so that final concentration was 500 mg/ml (50 ug total).

3) All tubes were incubated at 37° C. for 30 minutes (GEN probe run according to protocol).

4) 200 μL of water was added to each tube to bring volume up to 300 μL, then 2 Phenol/Chloroform extractions were performed (including GEN Probe).

5) 30 μL of 3M sodium acetate and 600 μL ethanol was added to the aqueous layer, and this mixture incubated at −20° C. over the weekend.

6) Samples were spun at 4° C. for thirty minutes, excess ethanol was removed, and pellets were dried in the Lyophillizer for 1 hour.

7) Samples were resuspended into 20 μL TE + 3 μL loading buffer and electrophoresed for 35 minutes at 150 V (94 VH)(1% agarose gel in 1× TAE buffer) (40mM TRIS acetate/1 mM EDTA).

8) Gel was ethidium bromide stained (1 μg/1 ml) and visualized under UV light.

Results show achromopeptidase released DNA of a distinct 23,000 base pair size. No other enzymes released much DNA.

EXAMPLE 4

This experiment screens a second set of enzymes for the ability to lyse *M. tuberculosi* while preserving the DNA for possible detection procedures.

Materials

*M. tuberculosis*
Gen probe lysing tube

Enzymes

1. Achromopeptidase
2. O—Glycanase (Genzyme (Boston, Mass.) Code O-ASE Lot #39178)
3. Lyticase (from *Arthrobacter lureus* Sigma Cat #L-8137 Lot # 69F-6819)
4. Hyaluronidase (Type VI-S Sigma Cat #H-3631 Lot #88F-807
5. Thermolysin (Protease Type X from *Bacillus Thermoproteclyticus rokko* Sigma Cat #P-1512 Lot #978-0833
6. α-L-Fucosidase (Bohringer Mannheim, Indianapolis, Ind. Cat #104945 Lot #1109822-10)

Procedure

Samples were processed in same manner as those in Example 3. Basically: 2 ml of *M. tuberculosis* used per sample. Samples reconstituted into 100 µl of enzyme in H₂O at 500 µg/ml (50 µg total) concentration, all samples incubated at 37° C. 30 minutes. Gen-probe was run as a control (which involved sonicating 15 minutes at 60° C.). Two phenol/chloroform extractions were performed except one extra was done with the fucosidase sample, samples were precipitated in ethanol, lyophillized, resuspended in TE buffer and run on a 1% agarose gel, followed by ethidium bromide staining.

The visual results indicate the enzyme achromopeptidase liberates more DNA than other enzymes.

EXAMPLE 5

This experiment optimizes pH and buffer conditions for lysis of mycobacteria using achromopeptidase.

Materials

*M. tuberculosis*
Bactec bottle #16
Achromopeptidase (Sigma Cat# A-3547 Lot #88F-0799)
Trizma 7.0 (E Cat #3503 Lot #89F-5615
Trizma 8.0 (Sigma Cat #T-4753 Lot #28F-5628)
Boric Acid (Aldrich, Milwaukee, Wisc. Cat #26,646-2 Lot #3501TJ)
Sodium Chloride (Sigma Cat # S-9625 Lot #27F-6086)
Phenol:chloroform 1:1 tris saturated
70% ethanol (Baxter, Charlotte, NC B+J brand Lot #E-K476
3M sodium acetate pH 5.2
Freeze drying unit (Virtis model)
Electrophoresis equipment
The following 4 buffers were prepared in 50 ml amounts:
1. 100 mM Trizma pH 7.0+10 mM NaCl
2. 100 mM Trizma pH 8.0+10 mM NaCl
3. 100 mM Trizma pH 9.0+10 mM NaCl
4. 60 mM Borate pH 9.0+10 mM NaCl Four 2 ml aliquots of *M. tuberculosis* were harvested and the pellets resuspended in 1 ml of each buffer.

Ten µl of a 5 mg/ml solution of achromopeptidase in H₂O was added to each 1 ml aliquot (50 µg total).

All samples were incubated at about 50° C. 30 minutes, vortexing several times during incubation.

Each sample was subjected to two phenol/chloroform extractions, followed by an overnight incubation at −20° C. with 2 volumes ethanol and 1/10 volume 3M sodium acetate.

DNA was precipitated and pellet was dried in a speed vaccuum, resuspended in TE tracing dye and run on agarose gel.

Results show that Trizma 9.0+10 mM NaCl is the best buffer. More DNA is seen using this buffer than the others.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

We claim:

1. A method for lysing Mycobacteria which consists essentially of exposing the Mycobacteria to a lysis effective amount of the enzyme achromopeptidase for a time and under conditions for lysis.

2. The method of claim 1 in which the lysis effective amount of achromopeptidase is from about 50 to about 1000 units in about 25 to about 2500 microliters.

3. The method of claim 2 in which the lysis effective amount of achromopeptidase is from about 100 to about 300 units in about 100 to about 500 microliters.

4. The method of claim 1 in which the Mycobacteria is selected from the group consisting of *Mycobacterium avium, Mycobacterium gordonae, Mycobacterium tuberculosis, Mycobacterium kansasii, Mycobacterium fortuitum, Mycobacterium chelonae, Mycobacterium bovis, Mycobacterium scrofulaceum, Mycobacterium paratuberculosis, Mycobacterium phlei, Mycobacterium marinum, Mycobacterium simiae, Mycobacterium szulgai, Mycobacterium intracellulare, Mycobacterium laprae, Mycobacterium xenopi, Mycobacterium ulcerans, Mycobacterium lepraemurium, Mycobacterium flavescens, Mycobacterium terrae, Mycobacterium nonchromogenicum, Mycobacterium malmoense, Mycobacterium asiaticum, Mycobacterium vaccae, Mycobacterium gastri, Mycobacterium triviale, Mycobacterium haemophicum, Mycobacterium africanum, Mycobacterium thermoresistable,* and *Mycobacterium smegmatis.*

5. The method of claim 4 in which the Mycobacteria is *Mycobacterium tuberculosis.*

6. The method of claim 4 in which the Mycobacteria is *M. bovis.*

7. The method of claim 4 in which the Mycobacteria is *Mycobacterium africanum.*

8. The method of claim 4 in which the Mycobacteria is *Mycobacterium intracellularae.*

9. The method of claim 4 in which the Mycobacteria is *Mycobacterium avium.*

10. The method of claim 4 in which the Mycobacteria is *Mycobacterium leprae.*

11. The method of claim 4 in which the Mycobacteria is *Mycobacterium chelonae.*

12. The method of claim 4 in which the Mycobacteria is *Mycobacterium paratuberculosis.*

13. A method of isolating cellular components of Mycobacteria which consists essentially of exposing the Mycobacteria to a lysis effective amount of the enzyme achromopeptidase for a time and under conditions for lysis and isolating cellular components.

14. The method of claim 13 in which the cellular component isolated is DNA.

15. The method of claim 13 in which the cellular component isolated is RNA.

16. A method of amplifying Mycobacteria nucleic acid which consists essentially of exposing the Mycobacteria to a lysis effective amount of the enzyme achromopeptidase for a time and under conditions for lysis and amplifying Mycobacteria nucleic acid.

17. The method of claim 16 in which the nucleic acid is DNA.

18. The method of claim 16 in which the nucleic acid is RNA.

19. The method of claim 5 which further comprises the isolation of DNA.

20. The method of claim 6 which further comprises the isolation of DNA.

21. The method of claim 7 which further comprises the isolation of DNA.

22. The method of claim 8 which further comprises the isolation of DNA.

23. The method of claim 9 which further comprises the isolation of DNA.

24. A method for identifying Mycobacteria which consists essentially of exposing the Mycobacteria to a lysis effective amount of the enzyme achromopeptidase for a time and under conditions for lysis and adding a Mycobacteria identifying agent.

25. The method of claim 24 in which the Mycobacteria identifying agent is a nucleic acid probe.

26. The method of claim 25 in which the nucleic acid probe is deoxyribonucleic acid.

27. The method of claim 25 in which the nucleic acid probe is ribonucleic acid.

28. The method of claim 24 in which the Mycobacteria is obtained from the source selected from the group consisting of feces, sputum, blood, tissue, urine, and other body fluids.

29. A kit comprising a Mycobacteria identifying agent and a lysis effective amount of achromopeptidase.

30. The kit of claim 29 in which the Mycobacteria identifying agent is a nucleic acid probe.

31. The kit of claim 30 in which the nucleic acid probe is deoxyribonucleic acid.

32. The kit of claim 29 in which the nucleic acid probe is ribonucleic acid.

33. A method for lysing Mycobacteria which consists essentially of isolating Mycobacteria from a sample and exposing the Mycobacteria to a lysis effective amount of achromopeptidase for a time and under conditions for lysis.

34. The method of claim 4 in which the lysis effective amount of achromopeptidase is from about 50 to about 1000 units in about 25 to about 2500 microliters.

35. The method of claim 4 in which the lysis effective amount of achromopeptidase in from about 100 to about 300 units in about 100 to 500 microliters.

36. The method of claim 34 in which the Mycobacteria is selected from the group consisting of *Mycobacterium avium, Mycobacterium gordonae, Mycobacterium tuberculosis, Mycobacterium kansasii, Mycobacterium fortuitum, Mycobacterium chelonae, Mycobacterium bovis, Mycobacterium scrofulaceum, Mycobacterium paratuberculosis, Mycobacterium phlei, Mycobacterium marinum, Mycobacterium simiae, Mycobacterium szulgai, Mycobacterium intracellulare, Mycobacterium laprae, Mycobacterium xenopi, Mycobacterium ulcerans, Mycobacterium lepraemurium, Mycobacterium flavescens, Mycobacterium terrae, Mycobacterium nonchromogenicum, Mycobacterium malmoense, Mycobacterium asiaticum, Mycobacterium vaccae, Mycobacterium gastri, Mycobacterium triviale, Mycobacterium haemophicum, Mycobacterium africanum, Mycobacterium thermoresistable,* and *Mycobacterium smegmatis.*

37. The method of claim 33 in which the Mycobacteria is *Mycobacterium tuberculosis.*

38. The method of claim 33 in which the Mycobacteria is *Mycobacterium intracellulare.*

39. The method of claim 33 which further comprises isolation of cellular components.

40. The method of claim 4 which further comprises amplification of nucleic acid.

41. The method of claim 4 which further comprises the addition of a Mycobacteria identifying agent.

42. The method of claim 38 in which the identifying agent is a nucleic acid probe.

* * * * *